United States Patent [19]

Rutledge

[11] 4,098,830
[45] * Jul. 4, 1978

[54] OXIDATIVE COUPLING OF ALKYLPHENOLS OR 1-NAPHTHOLS CATALYZED BY METAL COMPLEXES OF DICARBOXYLIC ACID COMPOUNDS

[75] Inventor: Thomas F. Rutledge, Wilmington, Del.

[73] Assignee: ICI Americas Inc., Wilmington, Del.

[*] Notice: The portion of the term of this patent subsequent to Jun. 20, 1995, has been disclaimed.

[21] Appl. No.: 770,209

[22] Filed: Feb. 18, 1977

[51] Int. Cl.$^2$ .............. C07C 27/00; C07C 37/00; C07C 41/00; C07C 45/00

[52] U.S. Cl. ................ 568/730; 260/396 N; 260/586 C; 260/590 E; 260/590 D; 260/590 FB; 260/613 R; 568/729; 568/719

[58] Field of Search .......... 260/620, 619 R, 619 B, 260/613 R, 396 N, 586 C, 590 E, 619 F

[56] References Cited

U.S. PATENT DOCUMENTS

| | | | |
|---|---|---|---|
| 2,057,676 | 10/1936 | Graves | 260/620 |
| 2,785,188 | 3/1957 | Coe | 260/620 |
| 2,885,444 | 5/1959 | Fookes et al. | 260/620 |
| 3,247,262 | 4/1966 | Kaeding | 260/620 |
| 3,322,838 | 5/1967 | Carrick et al. | 260/620 |
| 3,812,193 | 5/1974 | Randall et al. | 260/620 |
| 3,813,445 | 5/1974 | Masni | 260/620 |
| 3,873,627 | 3/1975 | Lee et al. | 260/620 |
| 3,876,709 | 4/1975 | Lee et al. | 260/620 |
| 4,008,266 | 2/1977 | Intelle | 260/620 |

FOREIGN PATENT DOCUMENTS

| | | | |
|---|---|---|---|
| 536,277 | 10/1931 | Fed. Rep. of Germany | 260/620 |
| 7,330,157 | 9/1973 | Japan | 260/620 |
| 467,058 | 2/1976 | U.S.S.R. | 260/620 |

OTHER PUBLICATIONS

White et al., I "J. of Poly. Sc.", Part A1, 8:1427–1438, (1970).
White et al., II "J. of Poly Sci.", Part A1 10:1565–1578 (1972).
Kaeding, "J. Org. Chem.", 28:1063–1067 (1963).

*Primary Examiner*—Norman Morgenstern
*Attorney, Agent, or Firm*—H. Jolyon Lammers

[57] ABSTRACT

Carbon-carbon coupled self-condensation products obtained by the oxidative coupling of alkylphenols or 1-naphthols are prepared by contacting an aqueous mixture of an alkylphenol, alkoxyphenyl, or 1-naphthol with oxygen in the presence of sufficient alkaline material to sustain a pH in the range of 7.0–9.5 during the oxidative coupling reaction and a catalyst system comprising a cupric, cobaltous, manganous, nickelous, chromic or ferric chelate of a dicarboxylic acid compound.

The mixture may optionally contain a surfactant.

17 Claims, No Drawings

OXIDATIVE COUPLING OF ALKYLPHENOLS OR 1-NAPHTHOLS CATALYZED BY METAL COMPLEXES OF DICARBOXYLIC ACID COMPOUNDS

FIELD OF THE INVENTION

The present invention relates generally to an improved process for preparing self-condensation products, such as diphenoquinones, biphenols, dinaphthenoquinones and binaphthols from alkylphenols, alkoxyphenols and naphthols and to a catalyst composition for use in said process. More particularly, the invention relates to a method of preparing carbon-carbon coupled condensation products of alkylphenols, alkoxyphenols or 1-naphthols by contacting an aqueous mixture of the phenol or naphthol with oxygen or an oxygen-containing gas in the presence of optionally a surfactant, sufficient alkaline material to sustain a pH in the range of 7.0–9.5 during the oxidative coupling reaction and a catalyst system comprising a cupric, cobaltous, manganous, nickelous, ferric or chromic complex of a dicarboxylic acid.

DESCRIPTION OF THE PRIOR ART

It is well known in the art that substituted phenols can be oxidized to yield self-condensation products, including diphenoquinones, biphenols and polyphenoxy ethers. The procedure employed in the preparation of these derivatives is generally referred to as the oxidative coupling of phenols.

The self-condensation products resulting from these oxidative coupling reactions can be catagorized as either the result of carbon-carbon coupling or carbon-oxygen coupling of said phenols. Diphenoquinones and biphenols are prepared by carbon-carbon coupling in accordance with the following general reactions depending upon the reactive sites available in the phenol employed.

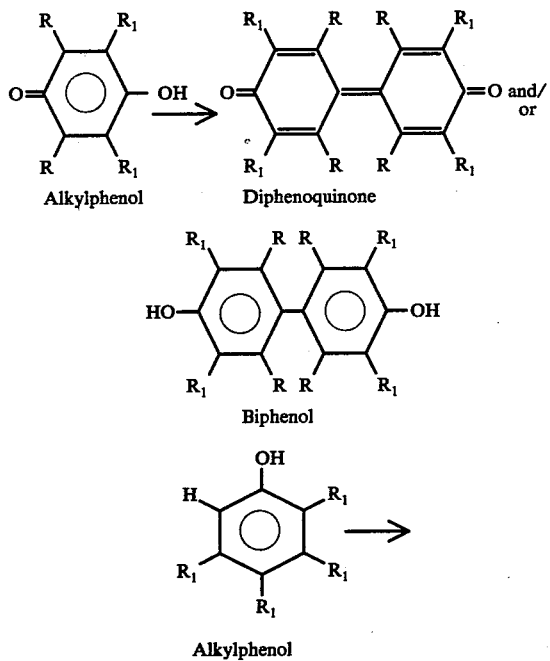

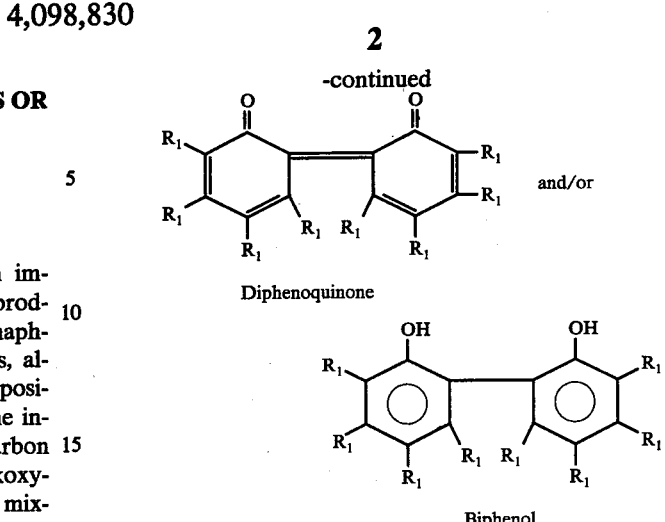

wherein R is hydrogen or $R_1$ and wherein $R_1$ is either alkyl, alkoxy, or another substituent all of which are well known in the art.

Similarly, polyphenoxy ethers are prepared by carbon-oxygen coupling in accordance with reactions such as the following general reaction:

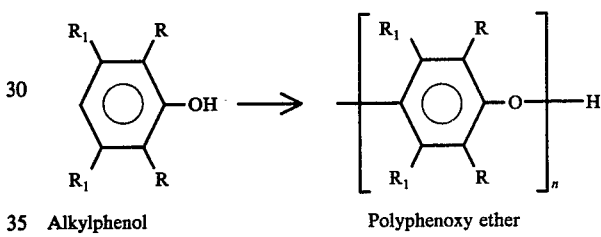

Alkylphenol    Polyphenoxy ether wherein R and $R_1$ are as defined above and $n$ is an integer.

A variety of materials, including metals and various salts and complexes thereof, have previously been disclosed as useful in promoting the oxidative coupling of alkylphenols. Thus, U.S. Pat. No. 2,785,188, discloses that copper powder may be utilized to prepare diphenoquinones from 2,6-dialkyl-4-halophenols. The use of cupric salts of carboxylic acids as the oxidizing agent in oxidative coupling reactions is disclosed in the art. See, in the regard, U.S. Pat. No. 3,247,262.

The use of manganese and cobalt compounds has also been disclosed in U.S. Pat. Nos. 3,337,501 3,573,257.

A variety of basic compounds have also been employed in oxidative coupling reactions. In many of these, such as those disclosed in U.S. Pat. Nos. 2,905,674 and 2,785,188, the function of the alkaline materials was to react with an acidic component, such as HCl, liberated during the course of the reaction and, therefore, a stoichiometric amount of the base was used.

It should be noted that, previous methods of preparing coupled products from alkyl- or alkoxy-phenols have required the use of either organic solvents or stoichiometric amounts of organic oxidizing reagents. The present invention provides for a metal dicarboxylic acid chelate catalyst system useful in the preparation of carbon-carbon coupled phenols or naphthols in an aqueous reaction medium. Also, with most of the prior art systems the resulting product or products were determined by the particular catalyst employed and could not easily be controlled. The present invention provides for a system which can be readily modified to produce either the biphenol or diphenoquinone directly from the reaction mixture.

In accordance with the present invention, it has been found that "alkyl- or alkoxy- phenols" and "1-naphthols" may be oxidatively coupled in a substantially basic aqueous medium if there is employed as a catalyst a system comprising a cupric, cobaltous, manganous, nickelous, ferric or chromic chelate of a dicarboxylic acid compound.

It has also been found that the type of product which is produced can be controlled by the amount of alkaline material and by the amount of catalyst employed in the catalyst system. By comparison, the prior art catalysts and processes employing said catalysts have a number of disadvantages which have restricted the utility of said catalysts and processes. These include (a) the requirement that the reaction be conducted in an organic solvent, (b) the fact that the primary product produced is often the polyphenoxy ether, and (c) the inability to form the biphenol, bisphenol or binaphthol derivative directly and in substantial quantities without requiring that this material be produced by a subsequent hydrogenation of the diphenoquinone, stilbenequinone or dinaphthenoquinone prepared in the oxidative coupling reaction. These disadvantages have been overcome by the use of the catalytic process of the present invention as is described in detail hereinafter.

SUMMARY OF THE INVENTION

In accordance with the present invention, condensation products such as diphenoquinones, stilbenequinones, bisphenols, biphenols, dinaphthenoquinones and binaphthols are selectively prepared by contacting a substantially basic aqueous mixture of an "alkylphenol", an "alkoxyphenol" or a "1-naphthol" with oxygen or an oxygen-containing gas in the presence of a catalyst composition comprising a cupric, cobaltous, manganous, nickelous, ferric or chromic complex of a dicarboxylic acid having the general structural formula:

HOOC—R—COOH wherein R is substituted or unsubstituted alkyl, aryl, aralkyl, alkaryl, or pyridyl provided that all substituents are inert during the formation of the chelate and in the oxidation reaction. In a preferred embodiment the aqueous mixtures additionally contain a surfactant. The phenols or naphthols, metal chelate complexes, and alkaline materials which may be utilized are critical to the present invention and are described in detail below.

Phenols/Naphthols

The phenols which may be employed in carrying out the present invention include both alkylphenols and alkoxyphenols. Specific phenols which may be utilized are described in detail below.

The alkylphenols which may be utilized are defined as any alkylphenol having at least two alkyl substituents, with the proviso that the phenols which have only two alkyl substituents must have the substituents in the ortho, ortho(2,6 in the formula below) or ortho, para (2,4 in the formula below) positions. These phenols are frequently referred to by the position of the alkyl substituent or substituents on the benzene ring as set forth in the following formula:

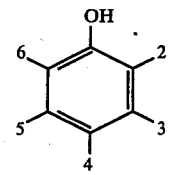

The process of the invention is applicable to any alkyl phenol having at least two alkyl substituents and steric properties such as to permit a coupling reaction. Thus if the para position is substituted with an alkyl group other than a methyl group, at least one ortho position must be unsubstituted. If one ortho and the para position are substituted, at least one of those substitutions must be a tertiary alkyl group. If both ortho positions are substituted, the para position must be either unsubstituted or substituted with a methyl group and no more than one meta position may be substituted with a tertiary alkyl group.

Thus, the alkylphenols will have one of the following formulas:

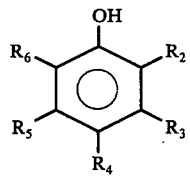

I wherein $R_2$ and $R_6$ are alkyl and $R_3$, and $R_5$ are hydrogen or alkyl, and $R_4$ is hydrogen or methyl with the proviso that $R_3$ and $R_5$ cannot both be tertiary alkyl.

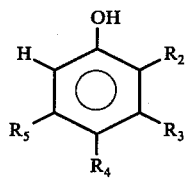

II wherein $R_2$ and $R_4$ are alkyl, provided that at least one of said alkyl groups is a tertiary alkyl and $R_3$ and $R_5$ are hydrogen or alkyl.

As used herein, the term alkyl refers to any monovalent radical derived from a saturated aliphatic hydrocarbon by removal of one hydrogen atom therefrom. The term includes both straight chain and branched chain materials containing from 1 to about 12 carbon atoms. Preferred results are achieved with alkylphenols wherein the alkyl substituent contains from 1 to about 5 carbon atoms.

The alkyl substituents are referred to herein as primary, secondary or tertiary alkyl depending upon the greatest number of carbon atoms attached to any single carbon atom in the chain.

Condensation products of any alkylphenol coming within the above-mentioned definition may be prepared in accordance with the present invention. As is apparent from that definition, the alkylphenols include dialkylphenols, trialkylphenols, and tetraalkylphenols. Specifically, the phenols which may be utilized include the following:

Ortho, para-substituted phenols including 2,4-dialkylphenols, 2,3,4-trialkylphenols, 2,4,5-trialkylphenols, and 2,3,4,5-tetraalkylphenols wherein the alkyl groups are either methyl or a primary, secondary, or tertiary alkyl provided that at least one of the alkyl groups in either the 2 or the 4 position is a tertiary alkyl, and ortho, ortho-substituted phenols including 2,6-dialkylphenols, 2,3,6-trialkylphenols and 2,3,5,6-tetraalkylphenols wherein the alkyl groups are either methyl or a primary, secondary, or tertiary alkyl provided that in the case of 2,3,5,6-tetraalkylphenols at least one of the alkyl groups in either the 3 or the 5 position is either a primary or secondary alkyl.

Representative ortho, para-substituted phenols which may be used include, for example 2,4-ditertiary-butylphenol, 2-methyl-4-tertiary-butylphenol, 2-tertiary-butyl-4-methylphenol, 2,4-ditertiary-amylphenol, 2,4-ditertiary-hexylphenol, 2-isopropyl-4-tertiary-butylphenol, 2-secondary-butyl-4-tertiary-butylphenol, 2-tertiary-butyl-3-ethyl-4-methylphenol, 2,5-dimethyl-4-tertiary-butylphenol, and 2-methyl-3-ethyl-4-tertiary-butylphenol.

Representative 2,6-dialkylphenols (ortho, orthosubstituted) include, for example 2,6-xylenol, 2-methyl-6-butylphenol, 2,6-diisobutylphenol, 2-octyl-6-methylphenol, 2-isobutyl-6-dodecylphenol, 2-ethyl-6-methylphenol, 2-methyl-6-tertiary-butylphenol, 2,6-diisopropylphenol, 2,6-disecondary-butylphenol, 2,6-ditertiary-butylphenol and 2-cyclohexyl-6-methylphenol.

Representative 2,3,6-trialkylphenols which may be utilized in accordance with the present invention include, for example, 2,3,6-trimethylphenol, 2,3,6-triethylphenol, 2,6-dimethyl-3-ethylphenol, 2,3-diethyl-6-tertiary-butylphenol.

Representative 2,3,5,6-tetraalkylphenols which may be utilized in accordance with the present invention include, for example 2,3,5,6-tetramethylphenol, 2,3,5-trimethyl-6-tertiary-butylphenol, 2,3,6-trimethyl-5-tertiary-butylphenol, 2,3-dimethyl-5,6-diethylphenol, and 2-methyl-3-ethyl-5-isopropyl-6-butylphenol.

When an ortho, para-substituted alkylphenol is employed the coupling reaction proceeds in accordance with the following reaction resulting in the o, o'-coupled product.

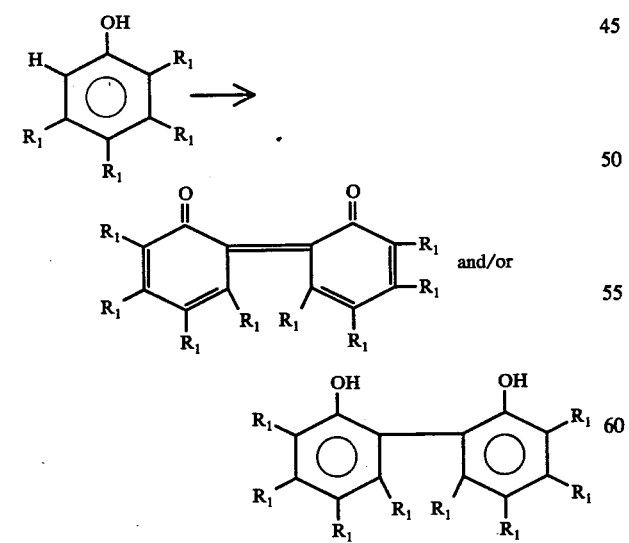

In this reaction each R represents hydrogen or an alkyl group as defined above depending upon whether di, tri, or tetra substituted alkylphenol is utilized.

Similarly, with the ortho, ortho-substituted alkylphenols, the reaction results in the p,p'-coupled product in accordance with the following reaction when R is hydrogen or alkyl depending upon which of the above-mentioned alkylphenols is used as the starting material.

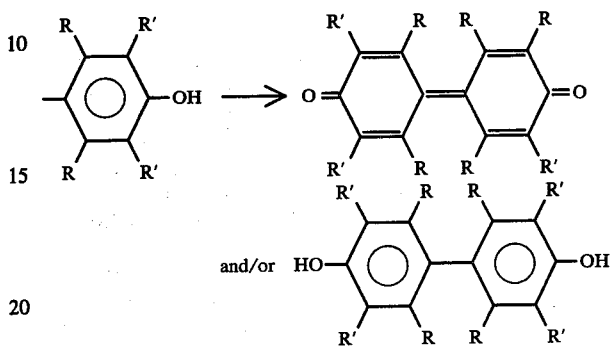

It has also been found that alkoxyphenols may be oxidatively coupled in accordance with the present invention. These include among others 2,6-disubstituted phenols wherein at least one of the substituents is an alkoxy group containing up to about six carbon atoms such as methoxy, ethoxy, propoxy, butoxy and pentoxy. In addition to the 2,6-dialkoxyphenols, 2-alkyl-6-alkoxyphenols, wherein the alkyl groups are as defined above for the alkylphenols, may be utilized. As used herein the term alkoxyphenols is intended to include both types of compounds. These compounds may be represented by the following general formulas:

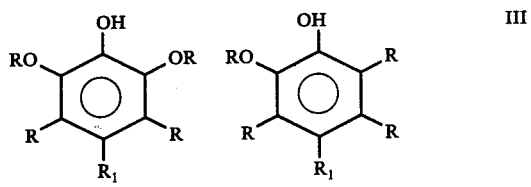

wherein each R is any alkyl group as defined above for the alkylphenols or OR and $R_1$ is either hydrogen or methyl, provided that the substituents adjacent to $R_1$ cannot both be tertiary alkyl or tertiary alkoxy. Representative alkoxyphenols which may be utilized include, for example, 2,6-dimethoxyphenol, 2,6-diethoxyphenol, 2,6-dibutoxyphenol, 2-methoxy-6-pentoxyphenol, 2-methyl-6-methoxyphenol and 2-ethyl-6-propoxyphenol, 2-methoxy-3-ethoxy-6-methylphenol.

When these phenols are utilized the reaction proceeds in accordance with the following representative reaction resulting in the p,p'-coupled material.

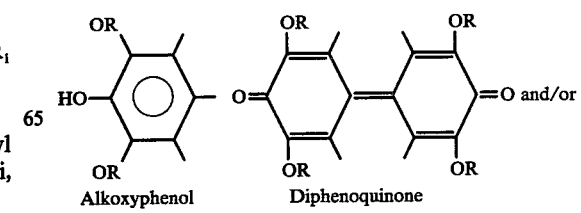

Alkoxyphenol       Diphenoquinone

-continued

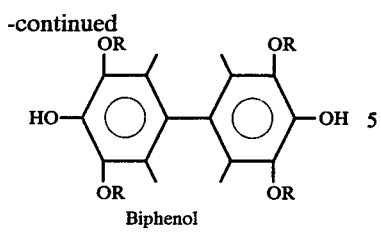
Biphenol

Mixtures of 2 different phenols may also be utilized. When this is done, there generally results a mixture of three different materials. Two of these are the products of the oxidative coupling of one molecule of one of the phenols with a second molecule of the same phenol. The third product is that resulting from the oxidative coupling of one molecule of the first phenol with one molecule of the second phenol. The products may be separated prior to use, as is well understood in the art.

Moreover, 1-naphthol and substituted 1-naphthols having at least 1 unsubstituted position ortho or para to the hydroxyl group may also be employed. The naphthols which may be coupled in accordance with the present invention are represented by the following general formula:

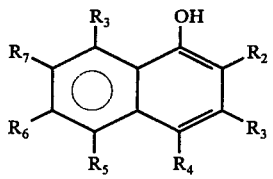

IV wherein
$R_2$, $R_3$ and $R_4$ are hydrogen, alkyl containing from 1 to 5 carbon atoms, or alkoxy containing from 1 to 6 carbon atoms, provided that either or both $R_2$ or $R_4$ are hydrogen and $R_5$, $R_6$, $R_7$, and $R_8$ are hydrogen, alkyl containing from 1 to 5 carbon atoms or alkoxy containing from 1 to 6 carbon atoms provided that tertiary alkyl or tertiary alkoxy groups may not be attached to adjacent carbon atoms of the naphthalene molecule.

Representative naphthols which may be utilized include, for example, 1-naphthol, 2-methyl-1-naphthol, 2,3-dimethyl-1-naphthol, 4-ethyl-1-naphthol, and 2-methoxy-1-naphthol.

When a naphthol is employed, the coupling reaction takes place in accordance with the following general reactions depending upon the reactive positions — i.e., those either ortho or para to the hydroxy group — available. Thus, if $R_2$ is hydrogen and $R_4$ is alkyl or alkoxy

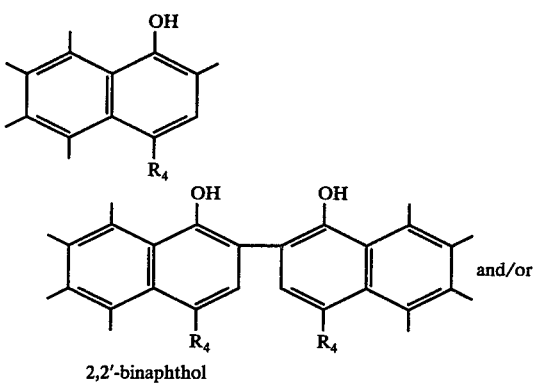

-continued

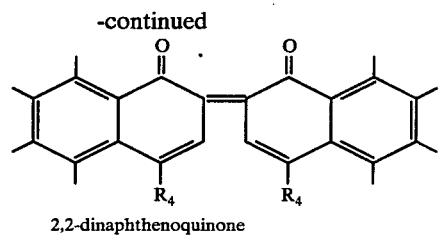
2,2-dinaphthenoquinone

Similarly, if $R_4$ is hydrogen and $R_2$ is alkyl or alkoxy, the products are the 4,4'-binaphthol and the 4,4'-dinaphthenoquinone. When both $R_2$ and $R_4$ are hydrogen the products may be a mixture of the 2,2'-; 2,4'- and 4,4'-binaphthols and dinaphthenoquinones.

Finally, the catalyst system of this invention may also be employed to prepare coupled products of alkylphenols wherein all of the positions ortho and para to the hydroxy group are substituted and the substituent para to the hydroxy group is methyl. These alkylphenols may be represented by the following general formula:

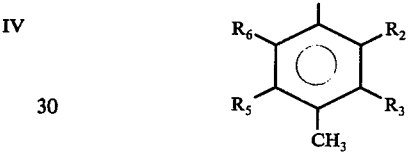

V wherein
$R_3$ is hydrogen, a primary, secondary, or tertiary alkyl or an alkoxy group:
$R_5$ is a primary or secondary alkyl group containing from 1–5 carbon atoms and $R_2$ and $R_6$ are a primary, secondary or tertiary alkyl or an alkoxy group.

Representative compounds which may be employed include, for example 2,4,6-trimethylphenol; 2,6-disecondary-butyl-4-methylphenol; 2-methyl-6-t-butyl-4-methylphenol; and 2,3,4,6-tetramethylphenol.

When one of these alkylphenols is employed the reaction proceeds in accordance with the following general reaction to produce the stilbenequinone or bisphenol derivative. These materials are useful in the same applications set forth above for the diphenoquinones, dinaphthenoquinones, biphenols and binaphthols

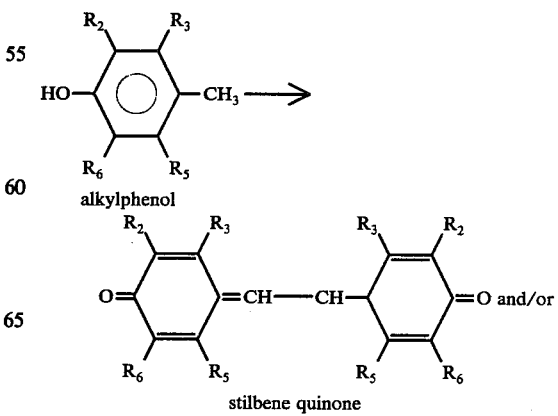

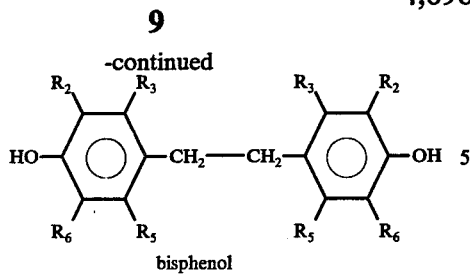

bisphenol where the values for the substituents are those specified in formula V.

It should be specifically noted that the term "alkyl phenol" is hereby defined as only those alkyl phenols of formulas I, II, and V and their isomers, the term "alkoxy phenol" is hereby defined as only those alkoxy phenols of formula III and their isomers and that the term "1-naphthols" is defined as only those 1-naphthols of formula IV and their isomers.

METAL COMPLEX'

One of the essential components of the catalyst system of the present invention is a metal chelate of a dicarboxylic acid By the term metal chelate or complex of a dicarboxylic acid is meant those complexes in which the metal cation group forms a bridge between the oxygen atoms of the two carboxylic acid groups. It is therefore important to appreciate that not all dicarboxylic acid compounds will form complexes useful in the process of the present invention. For example a amino substituted dicarboxylic acid may well have the amino group disposed such that the complex will be formed by bridging a carboxylic acid group through the metal cation to the amine group rather than to the second carboxylic group. A more detailed description of chelates or complexes may be found in Chemistry of the Coordination Compounds, by J.C. Bailar, Reinhold Publishers, N.Y. 1956. A preferred metal complex is the 5-membered ring $Cu^2.2$ oxalic acid complex whose structure may be represented by the following structure:

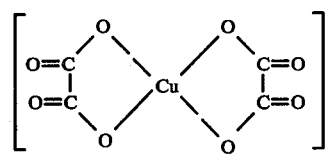

The metal source for the chelate is a cupric, manganous, nickelous, ferric, chromic or cobaltous ion which, may be conveniently added to the dicarboxylic acid compound as for example as acetates, formates or chlorides.

The dicarboxylic acids that have been found useful in the process of the present invention may be represented by the following structural formula:

wherein R has the aforementioned value.

Preferred aliphatic dicarboxylic acids compounds may be represented by the following formula:

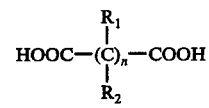

wherein $n$ is zero to 10 and $R_1$ and $R_2$ may each be hydrogen, lower alkyl, phenyl cyclohexyl, cyclopentyl, pyridyl or naphthyl and wherein the compound may contain olefinic double bonds.

Specific aliphatic acids include oxalic acid, malonic acid, succinic acid, and phenylmalonic acid.

Preferred aromatic carboxylic acid compounds include those represented by the following nine general formulas:

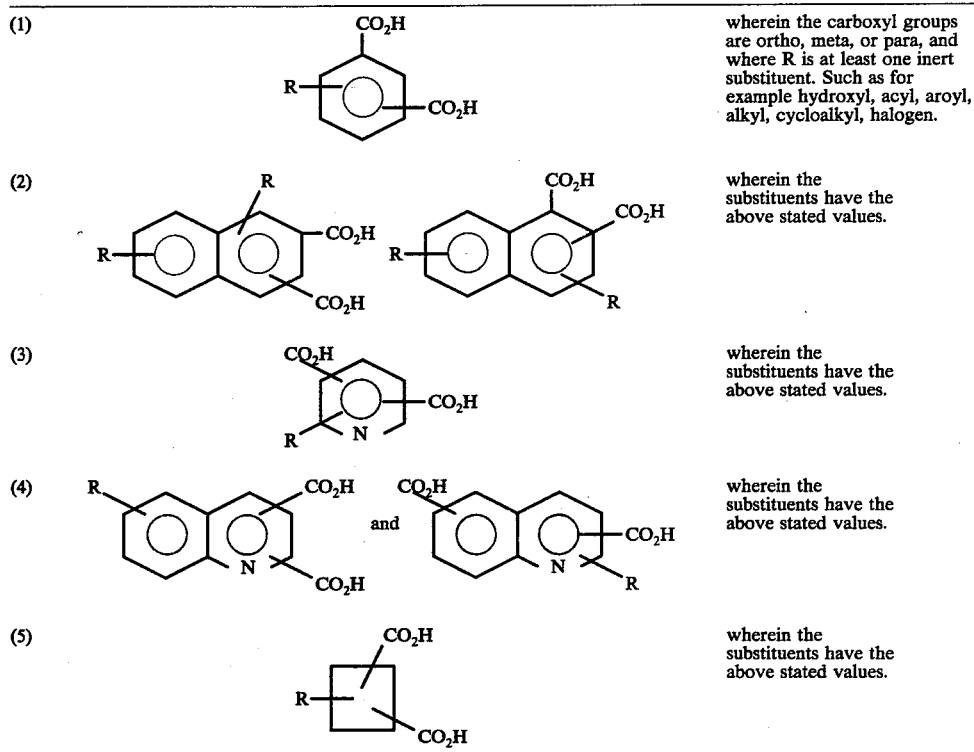

| | | |
|---|---|---|
| (6) | 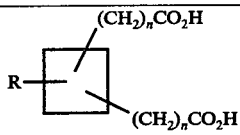 | wherein the substituents have the above stated values and n = 1 or 2. |
| (7) | 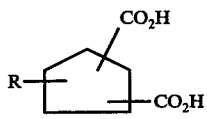 | wherein the substituents have the above stated values. |
| (8) | 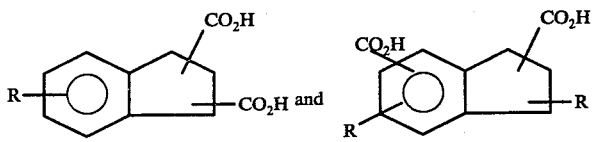 | wherein the substituents have the above stated values. |
| (9) | 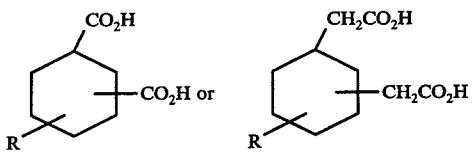 | wherein the substituents have the above stated values. |

Specific cyclic carboxylic acids include: o-phthalic acid, 2,3-naphthalenedicarboxylic acid, 2,3-pyridinedicarboxylic acid, 1,1-cyclobutanedicarboxylic acid, and 1,1-cyclobutanediacetic acid.

As shown above various inert substituents may be attached to the rings. The only proviso being that they are inert in the chelate formation reaction and do not take part in the oxidation reaction.

The metal chelates are prepared by reacting the dicarboxylic acids with a source of the appropriate metal ions. The metal ion source may include various metal salts including halides, halo hydroxides, carboxylates, acetates, nitrates, sulfates, alkyl sulfates, aryl sulfates, carbonates, hydroxides or chlorates.

Some of the chelates are commercially available but those that are not may be prepared in any manner and the preparation thereof has not been found to be critical to the present invention. Similarly the ratio of dicarboxylic acid to metal source has been found to be not narrowly critical. It should be noted however that if the ratio of dicarboxylic acid to metal source is less than one, less complex is formed. The following three methods have been employed but other methods, which will be readily apparent to those skilled in the art from the description of the invention given herein, may also be utilized.

First, suitable amounts of the dicarboxylic acid and a source of metal ions may be combined in a suitable medium such as water and reacted to form the chelate. The chelate is prepared by simply stirring the solution for a period of time. If desired, heat may be applied to accelerate formation of the chelate.

Alternatively, the dicarboxylic acid and the source of the metal ion may simply be combined and added to the reaction mixture wherein the chelate of the dicarboxylic acid is formed. When this is done any basic compound required to neutralize acidic by-products of the chelates forming reaction is also added directly to the reaction mixture.

Finally, the dicarboxylic acid, the source of metal ion, and any required basic compound may be added separately to the reaction medium and the complex formed in situ. As mentioned above, the method by which the metal complex is prepared has not been found to be critical to the present invention. However, further improved conversion results have been achieved when the source of metal ion and the dicarboxylic acid are combined prior to addition to the reaction medium.

The amount of metal chelate employed has not been found to be narrowly critical to the process of the present invention. However, it is preferred to employ at least 0.02 mmol of the chelate per 100 mmols of alkylphenol. If less than this amount is used the reaction is slower and the yields are low. Similarly, the maximum amount of chelate employed is not generally greater than 1 mmol of the complex per 100 mmol of alkylphenol. At amounts much in excess of this the cost of the catalyst results in a uneconomic system. Higher levels of catalysts within the range of 0.02 to 1 mmol per 100 mmols of alkylphenols tend to favor diphenoquinone formation.

Although any of the above-mentioned metal chelate may be used, improved conversion results have been achieved with the cupric complexes of oxalic and phthalic acids.

As mentioned above, an advantage of the catalyst system and of the process of the present invention is that the reaction can be carried out in an aqueous medium instead of an organic solvent as has been used in prior art systems. However, it has not been found to be critical to the present invention to employ a water soluble metal complex. Thus, materials which are insoluble in water as well as those which are soluble may be utilized.

Surfactant

The catalyst composition of the present invention may also include, as an optional component thereof, a surfactant. The presence of a surfactant aids in the dispersion of the solid products thereby moderately improving conversion results. Additionally the surfactant allows for easier cleaning of large reactors. A variety of surfactants, also known as dispersants, are well known in the art and, as used herein, the term surfactant is intended to refer to organic compounds that contain in the molecule both hydrophobic and hydrophilic groups.

Surfactants are often classified, based on the hydrophilic (water liking) group which they contain, as either anionic, cationic, nonionic, or amphoteric. Any such surfactants may be employed in the present invention.

Surfactants are discussed in detail in the *Encyclopedia of Chemical Technology*, Kirk-Othmer, Second Edition Vol. 19 at pages 508–589, and any of the surfactants described therein may be utilized in the present invention.

The amount of surfactant employed has not been found to be critical to the utility of the catalyst system in carrying out the improved process of the present invention. However, if the use of a surfactant is desirable such as for example to increase the amount of carbon-carbon coupled product, there should be included in the reaction mixture at least about 0.2 mmol of surfactant per 400 mmol of phenol or naphthol. Preferred conversion results are achieved when the amount of surfactant employed is equal to from about 0.2 to about 0.6 mmol of surfactant per 400 mmol of phenol or naphthol. Additional amounts of the surfactant may be employed; however, the use of greater amounts of surfactant has usually not been found to significantly increase the total yield of product and it is, therefore, not generally desirable to include additional material in the reaction mixture. When a cupric alkyl sulfate as defined above is employed, both as the metal ion source and as the surfactant, the amount of said material employed is preferably equal to at least 0.2 mmol per 400 mmols of phenol or naphthol — i.e., the preferred amount of metal compound plus the preferred amount of surfactant.

Alkaline Material

In accordance with the present invention, an alkaline material is also included in the catalyst composition to ensure that the pH during the reaction is maintained in the range of 7.0–9.5. It has been found that the use of an alkaline material to raise the pH in the present system increases the conversion to carbon-carbon coupled products and decreases the conversion to carbon-oxygen coupled products. The use of such a material to maintain the required pH also increases the rate of the oxidative coupling reaction and decreases the amount of the metal compound which must be utilized.

The alkaline material useful in achieving the pH of the reaction and the improved results of the present invention is selected from the group consisting of alkali metal hydroxides, alkali metal carbonates, and alkali metal bicarbonates. The alkaline material may be added ether as a single compound or as a mixture of compounds. Representative materials which may be employed include, for example, sodium hydroxide, potassium hydroxide, lithium hydroxide, sodium carbonate, lithium carbonate, sodium bicarbonate, rubidium carbonate, rubidium hydroxide, cesium bicarbonate, and cesium hydroxide.

The amount of alkaline material employed has not been found to be narrowly critical to the present invention as long as the required pH range is maintained. However, preferred results are achieved when the amount of said material is equal to at least about 3 millimols per 100 mmols of phenol or naphthol. Smaller amounts of alkaline material will normally result in a reaction pH of less than 7.0 and will normally cause a low molar conversion of starting compound to final product. A preferred pH range is from about 7.5 to 9.0. Increased amount of alkaline material may also be utilized in carrying out the present invention. It has been found that, for a given set of reaction conditions, increasing the amount of alkaline material increases the total conversion to carbon-carbon coupled products and the relative amount of diphenoquinone, stilbenequinone, or dinaphthenoquinone as compared to the amount of biphenol, bisphenol or binaphthol. Thus, by varying the amount of alkaline material to vary the pH within the required pH range of 7.0–9.5, the type of product can be controlled.

Besides the selective production of carbon-carbon coupled products, an additional advantage of the catalyst system of the present invention is the ability to control the type of carbon-carbon coupled product produced. Thus, it is possible to prepare selectively either diphenoquinone or biphenol, stilbenequinone, or bisphenol, or dinaphthenoquinone or binaphthol, in accordance with the present invention. This result is achieved by controlling the amount of alkaline material included in the system. Generally, as the amount of alkaline material is increased, the percentage of quinone derivative produced also increases. Therefore to obtain larger amount of biphenolic product as opposed to quinone derivatives it is desirable to use sufficient alkaline material to raise the pH of the reaction material to a range of about 7.0–9.5, preferably 8.5–9.0. Higher pH values usually result in significant levels of oligomer formation. (carbon-oxygen coupled products).

Reaction Conditions

As mentioned above, an advantage of the catalyst system and process of the present invention is that it makes it possible for the oxidative coupling reaction to be carried out in an aqueous medium. The amount of water employed has not been found to be critical to the present invention and any amount of water which will permit the reaction mixture to be stirred during the course of the reaction may be employed. It should also be noted again that it is not essential that the various components be soluble in water and the term aqueous mixture as used herein is intended to include solutions, slurries, suspensions and the like.

The components of the reaction mixture may be combined in any suitable manner. Thus, the phenol or naphthol, surfactant, metal complex, alkaline material and water may be combined in any order in a suitable reaction vessel. Alternatively, and in a preferred method, the phenol or naphthol and optionally the surfactant are combined in water in a suitable reaction vessel, the mixture is stirred rapidly, preferably by utilizing a stainless steel impeller turning at 3,000–8,000 RPM and an aqueous mixture of the metal salt compound and dicarboxylic acid is added, followed by an aqueous solution of the alkaline material to maintain desired pH. In modifications of this procedure the metal complex may be added prior to heating or the metal complex and some alkaline material may particularly at low pH ranges be combined prior to addition to the reaction mixture.

The reaction mixture comprising phenol or naphthol, water metal complex and alkaline material is contacted with a suitable oxidizing agent to convert the phenol or naphthol to the desired product. Oxidizing agents which may be employed in carrying out the present invention include oxygen either alone or as an oxygen-containing gas, such as air. The oxygen may be introduced into the reaction mixture either directly as oxygen gas or as an oxygengenerating material such as ozone, hydrogen peroxide, or an organic peroxide. The amount of oxygen utilized should be sufficient to obtain the desired conversion of the phenol or naphthol to the coupled product. To assure that sufficient oxygen is present, oxygen should be introduced into the reaction mixture continuously during the course of the reaction.

The reaction conditions — i.e., time and temperature — employed have not been found to be narrowly critical to the process of the present invention. Preferred results have been achieved when the reaction mixture is maintained at from about 80° C. to 90° C. during the course of the reaction. However, temperatures above and below this preferred range may be utilized. At lower temperatures the reaction rate is reduced and at temperatures below about 40° C. it is so slow as to result in an uneconomic system. When operating at atmospheric pressure, as is desirable in some commercial operations, the practical upper limit on the temperature is 100° C., the boiling point of the water.

If the reaction is conducted at increased oxygen pressure, the reaction time is decreased, the total yield of coupled product is usually increased, and the relative amount of quinone derivative is also usually increased.

The amount of time required for completion of the reaction depends on the temperature employed and other variables such as the pressure, concentration of phenol or naphthol and the amount of metal complex, surfactant if present, and alkaline material employed. However, it has been found that, when conducted at atmospheric pressure, the reaction is usually completed in 6 hours or less.

Although, as mentioned above, the process of the present invention results primarily in the production of carbon-carbon coupled products, there are also sometimes included in the solids removed from the reaction mixture the following: (a) unreacted phenol or naphthol, and (b) low molecular weight polyphenoxy ether. The polyphenoxy ether and phenol or naphthol may be removed by washing the solids with a solvent in which these materials are soluble, such as an aromic hydrocarbon — e.g., xylene, toluene, benzene, or a halogenated solvent — e.g., methylene chloride. If it is desired to separate the materials from each other and from the solvent, this may be done by distillation.

If the reaction results in the mixture of biphenol and diphenoquinone, bisphenol and stilbene quinone, or binaphthol and dinaphthenoquinone, these materials may be separated by any method known in the art. An especially convenient way of separating the materials is to stir the solid product with a dilute aqueous solution of sodium hydroxide, which converts the biphenol, bisphenol or binaphthol to the sodium salt which is usually soluble in water. The insoluble diphenoquinone, stilbene quinone or dinaphthenoquinone may then be filtered off and the biphenol bisphenol or binaphthol recovered by adding the aqueous solution of the sodium salt thereof to a dilute solution of a strong acid such as hydrochloric acid from which the biphenol, bisphenol or binaphthol precipitates. Alternatively, the entire product may be hydrogenated or chemically reduced and converted to only the biphenol, bisphenol or binaphthol.

The diphenoquinones and/or biphenols as well as the binaphthols, bisphenols and dinaphthenoquinones and stilbene quinones produced in accordance with the present invention are suitable for any of the uses of these materials which have heretofore been described in the art. Thus, the diphenoquinones and dinaphthenoquinones may be used as inhibitors of oxidation, peroxidation, polymerization and gum formation in gasolines, aldehydes, fatty oils, lubricating oils, ethers and similar compounds as mentioned in U.S. Pat. No. 2,905,674 issued to Filbey. The diphenoquinones may also be hydrogenated, employing conventional techniques, to yield the corresponding biphenol. The biphenols may be employed as stabilizers in gasoline and other petroleum products as described in U.S. Pat. No. 2,479,948 issued to Luten et al. They may also be utilized as intermediates in the manufacture of such useful products as sulfones, carbonates, and epoxy resins. In order to describe the present invention so it may be more clearly understood the following examples are set forth. These examples are given primarily for the purpose of illustration and any enumeration of detail contained therein should not be interpreted as a limitation on the concept of the present invention.

In the examples the products are analyzed for weight percent of the corresponding diphenoquinone. The amount of corresponding biphenol was arrived at by subtracting the diphenoquinone amount from the theoretical 100% carbon-carbon coupled composition of the product.

EXAMPLE 1

Into a first flask there were added:
0.4 grams (2 mmols) of cupric acetate $Cu(OAc)_2 \cdot H_2O$,
0.26 grams (2 mmols) of 97% oxalic acid dihyrate,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper oxalic acid complex solution prepared above. The resulting mixture was stirred for 5 minutes and heated to 80° C. 1.58 grams of sodium hydroxide (as 39.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Thermo-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.6 grams of the product was obtained as a green solid which contained 30.6 wt. percent of the diphenoquinone and 69+ wt. percent of the biphenol.

EXAMPLE 2

Into a first flash there were added:
0.4 grams (2 mmols) of cupric acetate Cu(OAc)$_2$.-H$_2$O,
0.21 grams (2 mmols) of 99% malonic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper malonic acid complex solution prepared above. The resulting mixture was stirred for 5 minutes and heated to 80° C. 1.78 grams of sodium hydroxide (as 44.6 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.7 grams of the product was obtained as a green solid which contained 41.0 wt. percent of the diphenoquinone and 58+ wt. percent of the biphenol.

EXAMPLE 3

Into a first flask there were added:
0.2 grams (1 mmol) of cupric acetate Cu(OAc)$_2$.H$_2$O,
0.12 grams (1 mmol) of 99% succinic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 200 grams of deionized water and 48.8 grams (400 mmols) of 2,6-xylenol.

To the resulting slurry which was stirred using a Labline cruciform stainless steel impeller turning at about 6,000 rpm there was added the stirred copper succinic acid complex solution prepared above. The resulting mixture was stirred for 5 minutes and heated to 80° C. 1.34 grams of sodium bicarbonate (as 16 ml of 1.0 N) solution was added over a period of 3 minutes. At this point the pH of the mixture was found to be 6.7. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature, filtered to remove the water phase, and washed twice with 175 ml water. The water phase had a pH of 8.4. A sample of the solid was removed, dissolved in acetone and analyzed by gas-liquid chromatography. The analysis indicated that 44 mol percent of the 2,6-xylenol was unreacted.

The solid product was then washed with xylene to remove xylenol oligomer and dried at 60° C. overnight. 20.2 grams of the product was obtained as a yellow solid which contained almost none of the diphenoquinone and 99.0 wt. percent of the biphenol.

EXAMPLE 4

Into a first flask there were added:
0.4 grams (2 mmols) of cupric acetate Cu(OAc)$_2$.-H$_2$O,
0.24 grams (2 mmols) of 97% maleic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 200 grams of deionized water and 48.8 grams (400 mmols) of 2,6-xylenol.

To the resulting slurry which was stirred using a Labline cruciform stainless steel impeller turning at about 6,000 rpm there was added the stirred copper maleic acid complex solution prepared above. The resulting mixture was stirred for 5 minutes and heated to 80° C. 1.34 grams of sodium bicarbonate (as 16 ml of 1.0 N) solution was added over a period of 3 minutes. At this point the pH of the mixture was found to be 6.9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature, filtered to remove the water phase, and washed twice with 175 ml water. The water phase had a pH of 9.1. A sample of the solid was removed, dissolved in acetone and analyzed by gas-liquid chromatography. The analysis indicated that 47.7 mol percent of the 2,6-xylenol was unreacted.

The solid product was then washed with xylene to remove xylenol oligomer and dried at 60° C. overnight. 20.2 grams of the product was obtained as a yellow solid which contained almost none of the diphenoquinone and 99.0 wt. percent of the biphenol.

EXAMPLE 5

Into a first flask there were added:
0.4 grams (2 mmols) of cupric acetate Cu(OAc)$_2$.-H$_2$O,
0.24 grams (2 mmols) of 97% maleic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper maleic acid complex solution prepared above. The resulting mixture was stirred for 5 minutes and heated to 80° C. 1.12 grams of sodium hydroxide (as 28 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, and washed twice with 175 ml water.

The solid product was then washed with xylene to remove xylenol oligomer and monomer and dried at 60° C. overnight. 38.6 grams of the product was obtained as a green solid which contained 36.8 wt. percent of the diphenoquinone and 63 wt. percent of the biphenol.

EXAMPLE 6

Into a first flask there were added:
0.4 grams (2 mmols) of cupric acetate $Cu(OAc)_2 \cdot H_2O$,
0.27 grams (2 mmols) of 99% glutaric acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 200 grams of deionized water and 48.8 grams (400 mmols) of 2,6-xylenol.

To the resulting slurry which was stirred using a Labline cruciform stainless steel impeller turning at about 6,000 rpm there was added the stirred copper glutaric acid complex solution prepared above. The resulting mixture was stirred for 5 minutes and heated to 80° C. 0.96 grams of sodium hydroxide (as 24 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, and washed twice with 175 ml water. A sample of the solid was removed, dissolved in acetone and analyzed by gas-liquid chromatography. The analysis indicated that 94.7 mol percent of the 2,6-xylenol had reacted.

The solid product was then washed with xylene to remove xylenol oligomer and dried at 60° C. overnight. 36.1 grams of the product was obtained as a yellow solid which contained almost none of the diphenoquinone and 97.0 wt. percent of the biphenol.

EXAMPLE 7

Into a first flask there were added:
0.4 grams (2 mmols) of cupric acetate $Cu(OAc)_2 \cdot H_2O$,
0.29 grams (2 mmols) of 99+% adipic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; .1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper adipic acid complex solution prepared above. The resulting mixture was stirred for 5 minutes and heated to 80° C. 1.15 grams of sodium hydroxide (as 28.8 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, and washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.0 grams of the product was obtained as a green solid which contained 48.5 wt. percent of the diphenoquinone and 51+ wt. percent of the biphenol.

EXAMPLE 8

Into a first flask there were added:
0.4 grams (2 mmols) of cupric acetate $Cu(OAc)_2 \cdot H_2O$,
0.35 grams (2 mmols) of suberic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; .1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper suberic acid complex solution prepared above. The resulting mixture was stirred for 5 minutes and heated to 80° C. 1.76 grams of sodium hydroxide (as 44 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, and washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 39.8 grams of the product was obtained as a green solid which contained 60.0 wt. percent of the diphenoquinone and 39+ mol percent of the biphenol.

EXAMPLE 9

Into a first flash there was added:
0.4 grams (2 mmols) of cupric acetate Cu(OAc)$_2$·H$_2$O,
0.37 grams (2 mmols) of 97% phenylmalonic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper phenylmalonic acid complex solution prepared above. The resulting mixture was stirred for 5 minutes and heated to 80° C. 1.26 grams of sodium hydroxide (as 31.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.1 grams of the product was obtained as a green solid which contained 43.6 wt. percent of the diphenoquinone and 56+ wt. percent of the biphenol.

EXAMPLE 10

Into a first flask there were added:
0.4 grams (2 mmols) of cupric acetate Cu(OAc)$_2$·H$_2$O,
0.27 grams (2 mmols) of 96% methylmalonic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper methylmalonic acid complex solution prepared above. The resulting mixture was stirred for 5 minutes and heated to 80° C. 1.14 grams of sodium hydroxide (as 28.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.3 grams of the product was obtained as a green solid which contained 50.6 wt. percent of the diphenoquinone and 49+ wt. percent of the biphenol.

EXAMPLE 11

Into a first flask there were added:
0.4 grams (2 mmols) of cupric acetate Cu(OAc)$_2$·H$_2$O,
0.27 grams (2 mmols) of 98% dimethyl malonic acid,
25 grams of ion exchanged water.

Into a 500 ml flask, fitted with a gas addition tube, aa condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper dimethyl malonic acid complex solution prepared above. The resulting mixture was stirred for 5 minutes and heated to 80° C. 0.48 grams of sodium hydroxide (as 12 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 40.3 grams of the product was obtained as a green solid which contained 15.3 wt. percent of the diphenoquinone and 84+ wt. percent of the biphenol.

EXAMPLE 12

Into a first flask there were added:
0.4 grams (2 mmols) of cupric acetate Cu(OAc)$_2$.-H$_2$O,
0.34 grams (2 mmols) of 99% ortho-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper o-phthalic acid complex solution prepared above. The resulting mixture was stirred for 5 minutes and heated to 80° C. 1.12 grams of sodium hydroxide (as 28 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 41.8 grams of the product was obtained as a green solid which contained 46.2 wt. percent of the diphenoquinone and 53+ wt. percent of the biphenol.

EXAMPLE 13

Into a first flask there were added:
0.4 grams (2 mmols) of cupric acetate Cu(OAc)$_2$.-H$_2$O,
0.34 grams (2 mmols) of 99% ortho-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 200 grams of deionized water and 48.8 grams (400 mmols) of 2,6-xylenol.

To the resulting slurry which was stirred using a Labline cruciform stainless steel impeller turning at about 6,000 rpm there was added the stirred copper o-phthalic acid complex solution prepared above. The resulting mixture was stirred for 5 minutes and heated to 80° C. 1.76 grams of sodium hydroxide (as 44 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.4 grams of the product was obtained as a green solid which contained 14.0 wt. percent of the diphenoquinone and 85+ wt. percent of the biphenol.

EXAMPLE 14

Into a first flask there were added:
0.4 grams (2 mmols) of cupric acetate Cu(OAc)$_2$.-H$_2$O,
0.34 grams (2 mmols) of 99% ortho-phthalic acid,
25 grams of ion exchanged water.

In a 500 ml flask, fitted with a gas addition tube, a condenser, a thermometer, and a stirrer capable of operating at speeds in the range of from about 3,000 to about 8,000 rpm there were added; 2 grams of sodium lauryl sulfate, 200 grams of deionized water and 48.8 grams (400 mmols) of 2,6-xylenol.

To the resulting slurry which was stirred using Labline cruciform stainless steel impeller turning at about 6,000 rpm there was added the stirred copper o-phthalic acid complex solution prepared above. The resulting mixture was stirred for 5 minutes and heated to 80° C. 0.36 grams of sodium hydroxide (as 9 ml of 1.0 N) solution was added during the course of the reaction to maintain the pH of the mixture at 8. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 95.7 mol percent of the 2,6-xylenol had reacted.

The solid product was then washed with xylene to remove xylenol oligomer and monomer and dried at 60° C. overnight. 38.4 grams of the product was obtained as a yellow solid which contained 2.8 wt. percent of the diphenoquinone and 97.0 wt. percent of the biphenol.

EXAMPLE 15

Into a first flask there were added:
0.1 grams (0.5 mmols) of cupric acetate $Cu(OAc)_2 \cdot H_2O$,
0.085 grams (0.5 mmols) of 99% ortho-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper o-phthalic acid complex solution prepared above. The resulting mixture was stirred for 5 minutes and heated to 80° C. 1.44 grams of sodium hydroxide (as 36 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.3 grams of the product was obtained as a green solid which contained 57.6 wt. percent of the diphenoquinone and 42+ wt. percent of the biphenol.

EXAMPLE 16

Into a first flask there were added:
0.4 grams (2 mmols) of cupric acetate $Cu(OAc)_2 \cdot H_2O$,
0.68 grams (4 mmols) of 99% ortho-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper o-phthalic acid complex solution prepared above. The resulting mixture was stirred for 5 minutes and heated to 80° C. 1.20 grams of sodium hydroxide (as 30 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 38.1 grams of the product was obtained as a green solid which contained 44.4 wt. percent of the diphenoquinone and 55+ wt. percent of the biphenol.

EXAMPLE 17

Into a first flask there were added:
0.4 grams (2 mmols) of cupric acetate $Cu(OAc)_2 \cdot H_2O$,
0.17 grams (1 mmols) of 99% ortho-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper o-phthalic acid complex solution prepared above. The resulting mixture was stirred for 5 minutes and heated to 80° C. 2.38 grams of sodium hydroxide (as 59.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 36.6 grams of the product was obtained as a green solid which contained 49.5 wt. percent of the diphenoquinone and 49+ wt. percent of the biphenol.

EXAMPLE 18

Into a first flask there were added:
0.4 grams (2 mmols) of cupric acetate $Cu(OAc)_2 \cdot H_2O$,
0.49 grams (2 mmols) of 99% 2,3-naphthalenedicarboxylic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper naphthalene dicarboxylic acid complex solution prepared above. The resulting mixture was stirred for 5 minutes and heated to 80° C. 1.64 grams of sodium hydroxide (as 41 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 99 mol percent of the 2,6-xylenol had reacted.

The solid product was then washed with xylene to remove xylenol oligomer and dried at 60° C. overnight. 35.9 grams of the product was obtained as a green solid which contained 58.0 wt. percent of the diphenoquinone and 41+ wt. percent of the biphenol.

EXAMPLE 19

Into a first flask there were added:
0.4 grams (2 mmols) of cupric acetate $Cu(OAc)_2 \cdot H_2O$,
0.34 grams (2 mmols) of 99% 2,3 pyridine dicarboxylic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper pyridine dicarboxylic acid complex solution prepared above. The resulting mixture was stirred for 5 minutes and heated to 80° C. 1.04 grams of sodium hydroxide (as 26 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 39.0 grams of the product was obtained as a green solid which contained 56.2 wt. percent of the diphenoquinone and 43+ wt. percent of the biphenol.

EXAMPLE 20

Into a first flask there were added:
0.4 grams (2 mmols) of cupric acetate $Cu(OAc)_2 \cdot H_2O$,
0.34 grams (2 mmols) of 99% 2,6-pyridine dicarboxylic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper pyridine dicarboxylic acid complex solution prepared above. The resulting mixture was stirred for 5 minutes and heated to 80° C. 1.08 grams of sodium hydroxide (as 27 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove oligomer and dried at 60° C. overnight. 36.0 grams of the product was obtained as a green solid which contained 4.0 wt. percent of the diphenoquinone and 96 wt. percent of the biphenol.

EXAMPLE 21

Into a first flask there were added:
0.4 grams (2 mmols) of cupric acetate $Cu(OAc)_2 \cdot H_2O$,
0.29 grams (2 mmols) of 99% 1,1-cyclobutanedicarboxylic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper cyclobutanedicarboxylic acid complex solution prepared above. The resulting mixture was stirred for 5 minutes and heated to 80° C. 1.60 grams of sodium hydroxide (as 40 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 37.8 grams of the product was obtained as a green solid which contained 51.1 wt. percent of the diphenoquinone and 48+ wt. percent of the biphenol.

EXAMPLE 22

Into a first flask there were added:
0.4 grams (2 mmols) of cupric acetate $Cu(OAc)_2 \cdot H_2O$,
0.38 grams (2 mmols) of 99% 1,1-cyclobutanediacetic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper cyclobutanediacetic acid complex solution prepared above. The resulting mixture was stirred for 5 minutes and heated to 80° C. 1.24 grams of sodium hydroxide (as 31 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-xylenol had reacted.

The solid product was then washed with xylene to remove xylenol oligomer and dried at 60° C. overnight. 39.4 grams of the product was obtained as a green solid which contained 68.4 wt. percent of the diphenoquinone and 31+ wt. percent of the biphenol.

EXAMPLE 23

Into a first flask there were added:
0.5 grams (2 mmols) of cobaltous acetate $Co(OAc)_2 \cdot 4H_2O$,
0.34 grams (2 mmols) of o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred cobalt phthalic acid complex solution prepared above. The resulting mixture was stirred for 5 minutes and heated to 80° C. 0.90 grams of sodium hydroxide (as 22.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 93.6 mol percent of the 2,6-xylenol had reacted.

The solid product was then washed with xylene to remove xylenol oligomer and dried at 60° C. overnight. 31.6 grams of the product was obtained as a green solid which contained 5.4 wt. percent of the diphenoquinone and 94+ wt. percent of the biphenol.

EXAMPLE 24

Into a first flask there were added:
0.36 grams (2 mmols) of nickelous bicarbonate Ni(HCO$_2$)$_2$.2H$_2$O,
0.34 grams (2 mmols) of o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred nickel phthalic acid complex solution prepared above. The resulting mixture was stirred for 5 minutes and heated to 80° C. 1.10 grams of sodium hydroxide (as 27.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 78.3 mol percent of the 2,6-xylenol had reacted.

The solid product was then washed with xylene to remove xylenol oligomer and dried at 60° C. overnight. 14.4 grams of the product was obtained as a yellow solid which contained none of the diphenoquinone and 99+ wt. percent of the biphenol.

EXAMPLE 25

Into a first flask there were added:
0.54 grams (2 mmols) of ferric chloride FeCl$_3$.6H$_2$O,
0.34 grams (2 mmols) of o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred iron phthalic acid complex solution prepared above. The resulting mixture was stirred for 5 minutes and heated to 80° C. 1.376 grams of sodium hydroxide (as 34.4 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 70.1 mol percent of the 2,6-xylenol had reacted.

The solid product was then washed with xylene to remove xylenol oligomer and dried at 60° C. overnight. 15.2 grams of the product was obtained as a yellow solid which contained none of the diphenoquinone and and 99+ wt. percent of the biphenol.

EXAMPLE 26

Into a first flask there were added:
0.54 grams (2 mmols) of chromic chloride CrCl$_3$.6H$_2$O.
0.34 grams (2 mmols) of o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred chromic phthalic acid complex solution prepared above. The resulting mixture was stirred for 5 minutes and heated to 80° C. 1.62 grams of sodium hydroxide (as 40.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 65.8 mol percent of the 2,6-xylenol had reacted.

The solid product was then washed with xylene to remove xylenol oligomer and dried at 60° C. overnight. 10 grams of the product was obtained as a yellow solid which contained none of the diphenoquinone and 99+ wt. percent of the biphenol.

EXAMPLE 27

Into a first flask there were added:
0.5 grams (2 mmols) of manganous acetate Mn(OAc)$_2$.4H$_2$O,
0.34 grams (2 mmols) of o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 48.8 grams (400 mmoles) of 2,6-xylenol.

To the resulting slurry which was stirred using a Labline cruciform stainless steel impeller turning at about 6,000 rpm there was added the stirred manganous phthalic acid complex solution prepared above. The resulting mixture was stirred for 5 minutes and heated to 80° C. 0.72 grams of sodium hydroxide (as 18 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 66.0 mol percent of the 2,6-xylenol had reacted.

The solid product was then washed with xylene to remove xylenol oligomer and dried at 60° C. overnight. 19.1 grams of the product was obtained as a yellow solid which contained none of the diphenoquinone and 99+ wt. percent of the biphenol.

EXAMPLE 28

Into a first flask there were added:
0.4 grams (2 mmols) of cupric acetate Cu(OAc)$_2$.-H$_2$O,
0.26 grams (2 mmols) of 97% oxalic acid dihydrate,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 42.0 grams (200 mmoles) of 98% 2,6-di-t-butylphenol.

To the resulting slurry which was stirred using a Labline cruciform stainless steel impeller turning at about 6,000 rpm there was added the stirred copper oxalic acid complex solution prepared above. The resulting mixture was stirred for 5 minutes and heated to 80° C. 0.40 grams of sodium hydroxide (as 10 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 35.0 mol percent of the 2,6-di-t-butylphenol had reacted.

The solid product was then air dried overnight. 23.3 grams of the product was obtained as an orange solid which contained 16.6 wt. percent of the diphenoquinone and 84 wt. percent tetra-t-butylbiphenol.

EXAMPLE 29

Into a first flask there were added:
0.4 grams (2 mmols) of cupric acetate Cu(OAc)$_2$.-H$_2$O,
0.26 grams (2 mmols) of 97% oxalic acid dihydrate,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 42.6 grams (200 mmoles) of 2,4-di-t-butylphenol.

To the resulting slurry which was stirred using a Labline cruciform stainless steel impeller turning at about 6,000 rpm there was added the stirred copper oxalic acid complex solution prepared above. The resulting mixture was stirred for 5 minutes and heated to 80° C. 0.64 grams of sodium hydroxide (as 16 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 90.6 mol percent of the 2,4-di-t-butylphenol had reacted.

The solid product was then air dried overnight. The air dried solid was triturated with ethanol then filtered. 25.5 grams of the product was obtained as a near-white solid which contained none of the diphenoquinone and 99 wt. percent of the ortho-tetra-t-butylbiphenol.

EXAMPLE 30

Into a first flask there were added:
0.4 grams (2 mmols) of cupric acetate Cu(OAc)$_2$.-H$_2$O,
0.34 grams (2 mmols) of 99% o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 31.2 grams (200 mmols) of 2,6-di-methoxyphenol.

To the resulting slurry which was stirred using a Labline cruciform stainless steel impeller turning at about 6,000 rpm there was added the stirred copper phthalic acid complex solution prepared above. The resulting mixture was stirred for 5 minutes and heated to 80° C. 4.40 grams of sodium hydroxide (as 110 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 2,6-dimethoxy phenol had reacted.

The solid product was then air dried overnight. 30.0 grams of the product was obtained as a red solid which contained 36.2 wt. percent of the diphenoquinone and 43+ wt. percent of the biphenol.

EXAMPLE 31

Into a first flask there were added:
0.4 grams (2 mmols) of cupric acetate $Cu(OAc)_2 \cdot H_2O$,
0.34 grams (2 mmols) of 99% o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 43.3 grams (300 mmols) of 1-naphthol.

To the resulting slurry which was stirred using a Labline cruciform stainless steel impeller turning at about 6,000 rpm there was added the stirred copper o-phthalic acid complex solution prepared above. The resulting mixture was stirred for 5 minutes and heated to 80° C. 2.60 grams of sodium hydroxide (as 65 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that all of the 1-naphthol had reacted.

The solid product was then washed with xylene to remove oligomer and dried at 60° C. overnight. 39.5 grams of the product was obtained as a dark solid which contained 99 wt. percent carbon-carbon coupled product.

EXAMPLE 32

Into a first flask there were added:
0.4 grams (2 mmols) of cupric acetate $Cu(OAc)_2 \cdot H_2O$,
0.34 grams (2 mmols) of 99% o-phthalic acid,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 27.7 grams (200 mmols) of 2,4,6-trimethylphenol.

To the resulting slurry which was stirred using a Labline cruciform stainless steel impeller turning at about 6,000 rpm there was added the stirred copper phthalic acid complex solution prepared above. The resulting mixture was stirred for 5 minutes and heated to 80° C. 1.62 grams of sodium hydroxide (as 40.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water.

The solid product was then air dried overnight. 19.2 grams of the product was obtained as an orange solid which contained mostly the bisphenol as indicated by infrared analysis.

EXAMPLE 33

Into a first flask there were added:
0.4 grams (2 mmols) of cupric acetate $Cu(OAc)_2 \cdot H_2O$,
0.26 grams (2 mmols) of 97% oxalic acid dihydrate,
25 grams of ion exchanged water.

Into a 500 ml flask, fitted with a gas addition tube, a condenser, a thermometer, and a stirrer capable of operating at speeds in the range of from about 3,000 to about 8,000 rpm there were added; 0.2 grams of sodium lauryl sulfate, 200 grams of deionized water and 33.5 grams (200 mmols) of 98% 2-methyl-6-t-butylphenol.

To the resulting slurry which was stirred using a Labline cruciform stainless steel impeller turning at about 6,000 rpm there was added the stirred copper oxalic acid complex solution prepared above. The resulting mixture was stirred for 5 minutes and heated to 80° C. 0.70 grams of sodium hydroxide (as 17.5 ml of 1.0 N) solution was added during the course of the reaction to maintain the pH of the mixture at 9. The mixture was stirred under oxygen. The oxygen flow was rapid at the beginning to flush the system. After about ½ hours, oxygen flow was reduced and maintained at a level sufficient to causes low bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature acidified to pH 3 with HCl, filtered to remove the water phase, washed twice with 175 ml water. A sample of the solid was removed, dissolved in acetone and analyzed by gas-liquid chromatography. The analysis indicated that 85 mol percent of the phenol had reacted.

The solid product was then washed with xylene to remove oligomer and dried at 60° C. overnight. 28.6 grams of the product was obtained as a red solid which contained 90 wt. percent diphenoquinone and about 9 wt. percent of the biphenol.

What is claimed is:

1. A method of preparing a condensation product of an "alkylphenol", an "alkoxyphenol" or a "1-naphthol", by an oxidative coupling reaction said method comprising contacting a mixture of the phenol or naphthol with oxygen or oxygen containing gas in the presence of sufficient amount of alkaline material to sustain pH in the range of about 7-9.5 during the oxidative coupling reaction and a catalyst system comprising a cupric, manganous, cobaltous, nickelous, ferric or chromic metal complex of a dicarboxylic acid compound.

2. A method as claimed in claim 1 wherein the dicarboxylic acid compound has the structural formula:

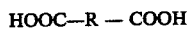

HOOC—R — COOH wherein R is a substituted or unsubstituted linear, branched or cyclic, aliphatic, or aromatic hydrocarbon or a heterocyclic ring containing N, O, or S.

3. A method, as claimed in claim 1 wherein the aqueous phenol mixture additionally comprises a surfactant.

4. A method, as claimed in claim 3 wherein the surfactant is sodium lauryl sulfate and is present in an amount equal to at least 0.005 mols per mol of phenol or naphthol.

5. A method, as claimed in claim 1, wherein the phenol is an "alkylphenol."

6. A method, as claimed in claim 5, wherein the "alkylphenol" is a 2,6-dialkylphenol.

7. A method, as claimed in claim 6, wherein the alkylphenol is 2,6-xylenol.

8. A method, as claimed in claim 5, wherein the alkyl groups of said "alkylphenol" contain from 1 to about 12 carbon atoms.

9. A method, as claimed in claim 5, wherein the alkyl groups of said "alkylphenol" contain from 1 to about 5 carbon atoms.

10. A method, as claimed in claim 1, wherein the catalyst system comprises a cupric: oxalic acid complex.

11. A method, as claimed in claim 10, wherein the "alkylphenol" is 2,6-xylenol.

12. A method, as claimed in claim 9, wherein the catalyst system is cupric: o-phthalic acid complex.

13. A method, as claimed in claim 1, wherein the amount of metal complex is equal to at least about 0.2 mmols per mol of phenol or naphthol.

14. A method, as claimed in claim 1, wherein the alkaline material is an alkali metal hyroxide.

15. A method, as claimed in claim 14, wherein the alkali metal hydroxide is sodium hydroxide.

16. A method, as claimed in claim 1, wherein the amount of alkaline material is equal to at least about 3 mmols per mol of phenol or naphthol.

17. A method, as claimed in claim 1, wherein the phenol is an alkylphenol having the following formula:

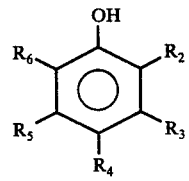

wherein $R_2$ and $R_6$ are alkyl and $R_3$ and $R_5$ are hydrogen or alkyl and $R_4$ is hydrogen or methyl.

* * * * *